(12) United States Patent
Taylor

(10) Patent No.: US 7,777,211 B2
(45) Date of Patent: Aug. 17, 2010

(54) SUBSTANTIALLY TRANSPARENT OBJECT DETECTION SYSTEM AND METHOD

(75) Inventor: Walter Taylor, Dale City, VA (US)

(73) Assignee: Dynex Technologies, Inc., Chantilly, VA (US)

( * ) Notice: Subject to any disclaimer, the term of this patent is extended or adjusted under 35 U.S.C. 154(b) by 33 days.

(21) Appl. No.: 11/832,578

(22) Filed: Aug. 1, 2007

(65) Prior Publication Data

US 2009/0032686 A1 Feb. 5, 2009

(51) Int. Cl.
*G01N 21/86* (2006.01)
*G02F 1/01* (2006.01)

(52) U.S. Cl. ................................ 250/559.4; 250/225

(58) Field of Classification Search .......... 250/226, 250/225, 559.09, 216, 559.4, 223 R, 223 B, 250/221; 356/33, 34, 308, 322, 327, 453, 356/239.1, 239.2, 239.4, 427–428
See application file for complete search history.

(56) References Cited

U.S. PATENT DOCUMENTS

| | | | | |
|---|---|---|---|---|
| 3,721,965 A | * | 3/1973 | Morgan-Voyce | 365/122 |
| 4,178,524 A | * | 12/1979 | Ritter | 310/304 |
| 5,141,110 A | * | 8/1992 | Trischan et al. | 209/524 |
| 5,670,118 A | | 9/1997 | Sponholtz | 422/102 |
| 5,715,048 A | | 2/1998 | Taylor | 356/229 |
| 6,016,192 A | | 1/2000 | Taylor | 356/229 |
| 6,212,949 B1 | | 4/2001 | Inder et al. | 73/304 R |
| 6,267,927 B1 | | 7/2001 | Pomar Longedo et al. | 422/65 |
| 6,717,675 B1 | * | 4/2004 | Munch | 356/429 |
| 6,855,901 B1 | * | 2/2005 | Guenard et al. | 209/577 |

* cited by examiner

*Primary Examiner*—Que T Le
*Assistant Examiner*—Don Williams
(74) *Attorney, Agent, or Firm*—Hayes Soloway P.C.

(57) ABSTRACT

A system for detecting the presence of a substantially transparent object includes a radiation source producing radiation at a predetermined bandwidth, and a radiation receiver is positioned to receive radiation from the radiation source. An opening is formed between the radiation receiver and the radiation source sized to allow a substantially transparent object such as a sample or reagent tip to slide between the radiation receiver and the radiation source. At least one polarizing filter is positioned between the radiation receiver and the opening, whereby a change in intensity of radiation received by the radiation receiver due to the presence or absence of the transparent object can be detected.

13 Claims, 7 Drawing Sheets

US 7,777,211 B2

SUBSTANTIALLY TRANSPARENT OBJECT DETECTION SYSTEM AND METHOD

FIELD OF THE INVENTION

The present invention is generally related to diagnostic devices, and, more particularly, automated and semi-automated immunoassay processing systems. The invention has particular utility in connection with an automated Enzyme-Linked ImmunoSorbent Assay (ELISA) processing apparatus, and will be described in connection with such utility, although other utilities are contemplated.

BACKGROUND OF THE INVENTION

Automatic apparatus for performing ELISA tests are commercially available. Such apparatus perform the tests on supports having a plurality of cells or wells for facilitating parallel and orderly processing of the samples. These supports, which are known as micro-titer plates, usually have a format of 8.0 times. 12 wells, for a total of 96 wells, and includes a robot capable of moving in X, Y and Z coordinates for picking and placing a sample or reagent tip, e.g., a pipette tip, in a well. However, occasionally, the apparatus may miss picking a sample or reagent tip. Since sample or reagent tips are essentially transparent to visible light, it is difficult to determine when a sample or reagent tip is missing.

SUMMARY OF THE INVENTION

The present invention provides improvements in automated and semi-automated immunoassay processing apparatus by providing a detection system for detecting the presence or absence of a sample or reagent tip in an automated assay processing system. More particularly, the present invention employs a radiation source producing radiation at a predetermined bandwidth. A radiation receiver is positioned to receive radiation from the radiation source. An opening is formed between the radiation receiver and the radiation source sized to allow a sample or reagent tip to slide between the radiation receiver and the radiation source. A first polarizing filter located between the radiation source and the opening, and a second polarizing filter is located between the radiation receiver and the opening. The first and second polarizing filters are rotated relative to one another so that when a sample of reagent tip is placed in the opening in the optical path, the sample or tip alters or depolarizes the radiation so that it is able to pass through the second polarizing filter to the radiation receiver.

The present invention can also be viewed as providing methods for detecting a substantially transparent object such as a sample or reagent tip within an automated assay processing system by passing a beam of light through a first polarizing filter, through the sample or reagent tip, and then through a second polarizing filter which is rotated relative to the first polarizing filter, and detecting a change in intensity of the light received at the radiation receiver.

BRIEF DESCRIPTION OF THE DRAWINGS

Other systems, methods, features, and advantages of the present invention will become apparent from the following detailed description taken in conjunction with the accompanying drawings, wherein like reference numerals designate corresponding parts and wherein.

DETAILED DESCRIPTION

Figure 1:
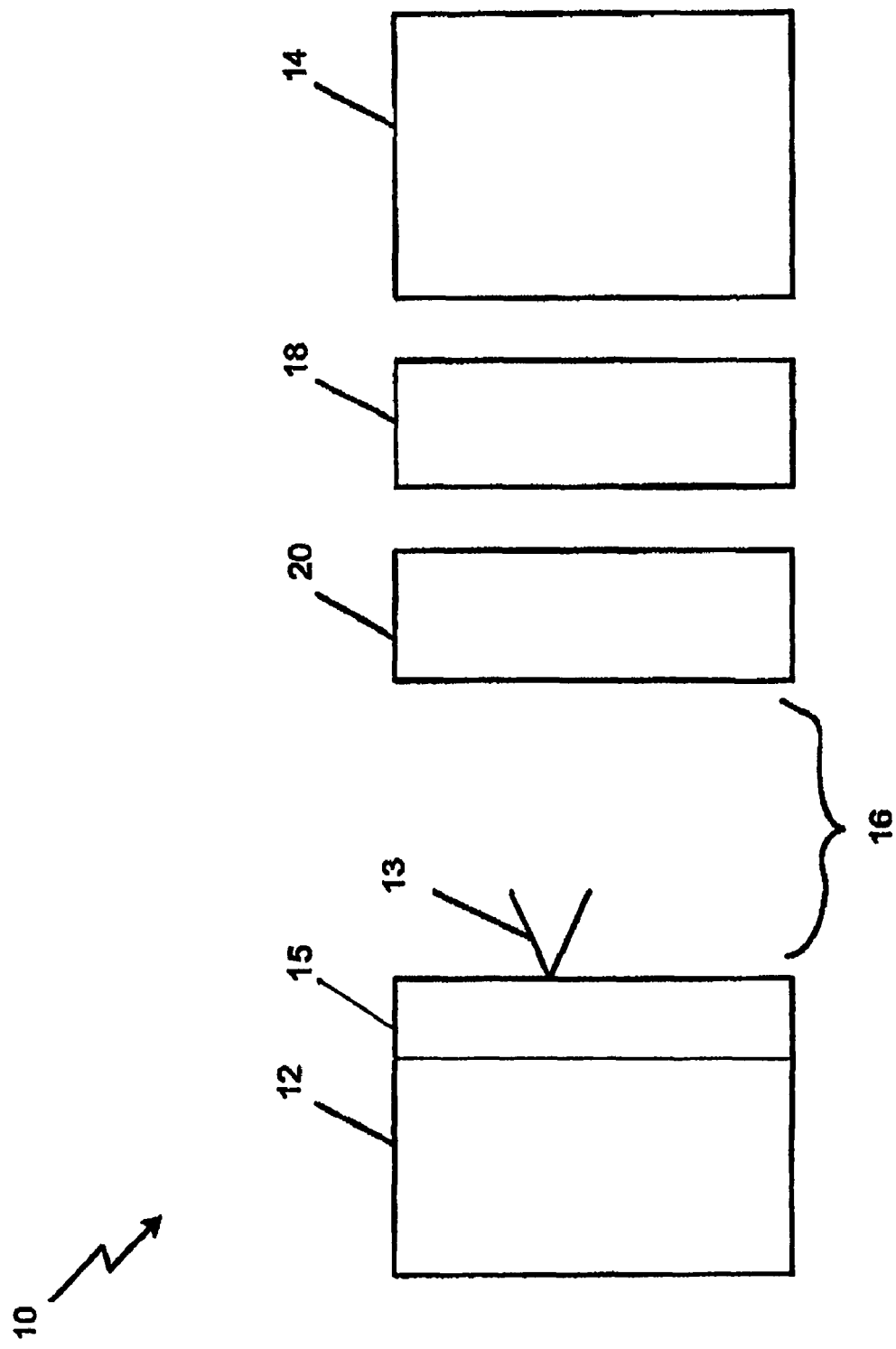
FIG. 1 is a schematic diagram of a substantially transparent object sensor, in accordance with a first exemplary embodiment of the present invention.

FIG. 1 is a schematic diagram of a substantially transparent object sensor 10, in accordance with a first exemplary embodiment of the present invention. The substantially transparent object sensor 10 includes a radiation source 12 producing radiation 13 at a predetermined bandwidth. A radiation receiver 14 is positioned to receive the radiation 13 from the radiation source 12. An opening 16 is formed between the radiation receiver 14 and the radiation source 12 and is sized to allow a substantially transparent object such as a sample or reagent tip to be positioned between the radiation receiver 14 and the radiation source 12. A bandpass filter 18 is located between the radiation receiver 14 and the opening 16. The bandpass filter 18 is transmissive for radiation 13 substantially within the predetermined bandwidth. A first polarizing filter 15 is located between the radiation source 12 and the opening 16, and a second polarizing filter 20, rotated relative to the first polarizing filter 15 is positioned between the radiation receiver 14 and the opening 16.

The substantially transparent object sensor 10 is useful for detecting substantially transparent objects between the radiation source 12 and the radiation receiver 14. As an example, the substantially transparent object may be a transparent or semi-transparent pipette tip. When a substantially transparent object such as a sample or reagent tip is placed within the opening 16, the substantially transparent object alters or depolarizes the radiation 13, which changes the intensity of radiation received at the radiation receiver 14.

Figure 2:
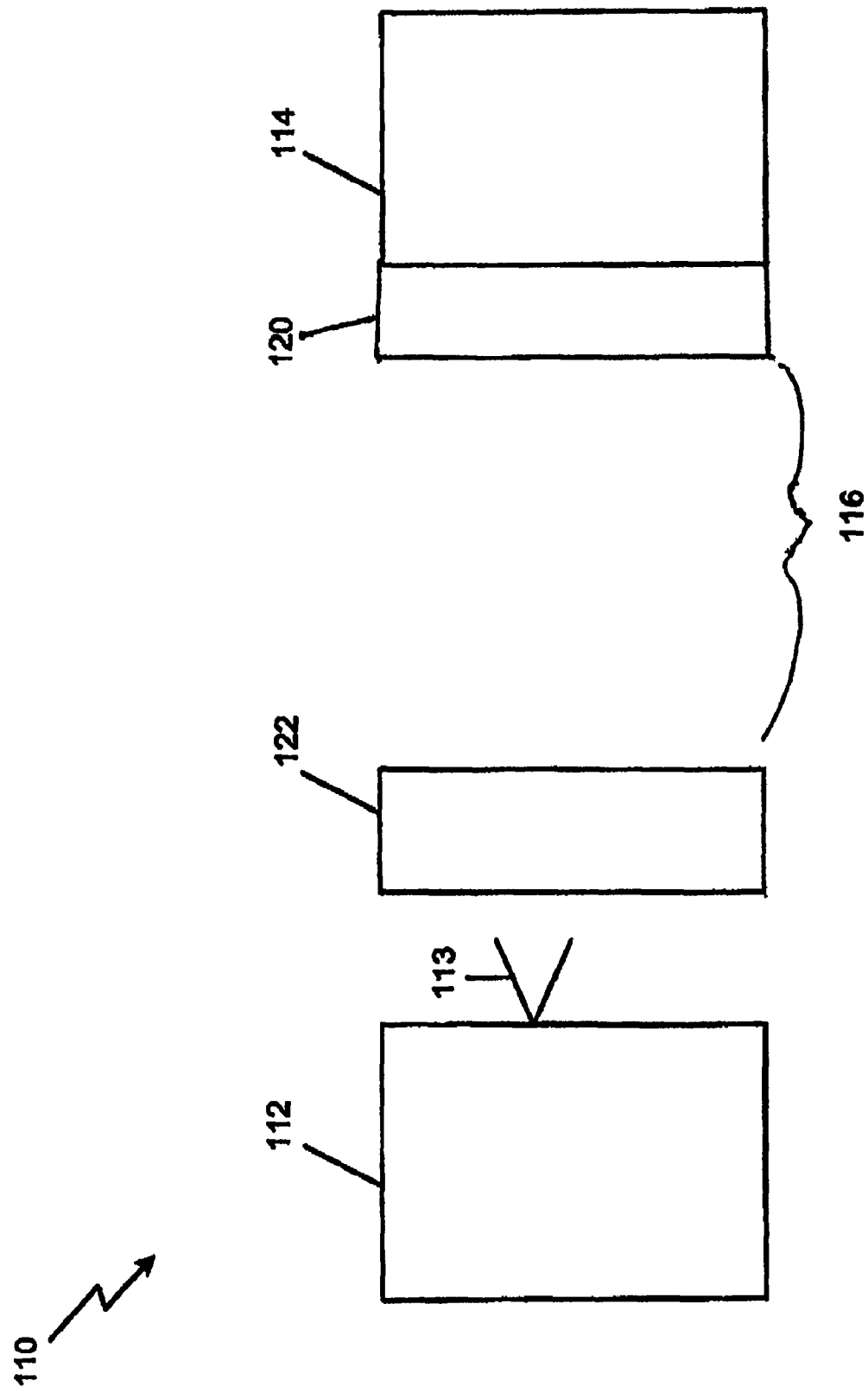
FIG. 2 is a schematic diagram of a substantially transparent object sensor, in accordance with a second exemplary embodiment of the present invention.

FIG. 2 is a schematic diagram of a substantially transparent object sensor 110, in accordance with a second exemplary embodiment of the present invention. The substantially transparent object sensor 110 includes a radiation source 112 producing radiation 113 at a predetermined bandwidth. A radiation receiver 114 is positioned to receive radiation from the radiation source 112. An opening 116 is formed between the radiation receiver 114 and the radiation source 112 sized to allow a substantially transparent object such as a sample or reagent tip to be slid between the radiation receiver 114 and the radiation source 112. A bandpass filter (not shown) is located between the radiation receiver 114 and the opening 116. The bandpass filter (not shown) is transmissive for radiation substantially within the predetermined bandwidth. Two polarizing filters 120, 122 are positioned between the radiation receiver 114 and the radiation source 112.

In the second exemplary embodiment, the bandpass filter is integral with the radiation receiver 114. More specifically, the radiation receiver 114 may be a pass band filtered photodiode. Further, the radiation source 112 may be a 660 nm LED and the radiation receiver 114 may be a 660 nm pass band-filtered photodiode.

In the second embodiment, a first polarizing filter 120 and a second polarizing filter 122 are rotated relative to one another, and positioned between the radiation receiver 114 and the radiation source 112. The first polarizing filter 120 may be positioned between the radiation receiver 114 and the opening 116, while the second polarizing filter 122 may be positioned between the radiation source 112 and the opening 116. In a preferred embodiment of the invention, the polarizing filters 120, 122 may be positioned orthogonally (90°) to each other to substantially block all radiation from reaching the radiation receiver 114 in normal operation. However, when a substantially transparent object is placed in the opening 116, radiation from the radiation source 112 is altered or depolarized such that a portion of the radiation is transmitted through the substantially transparent object and the first polarizing filter 120 to reach the radiation receiver 114.

Figure 3:
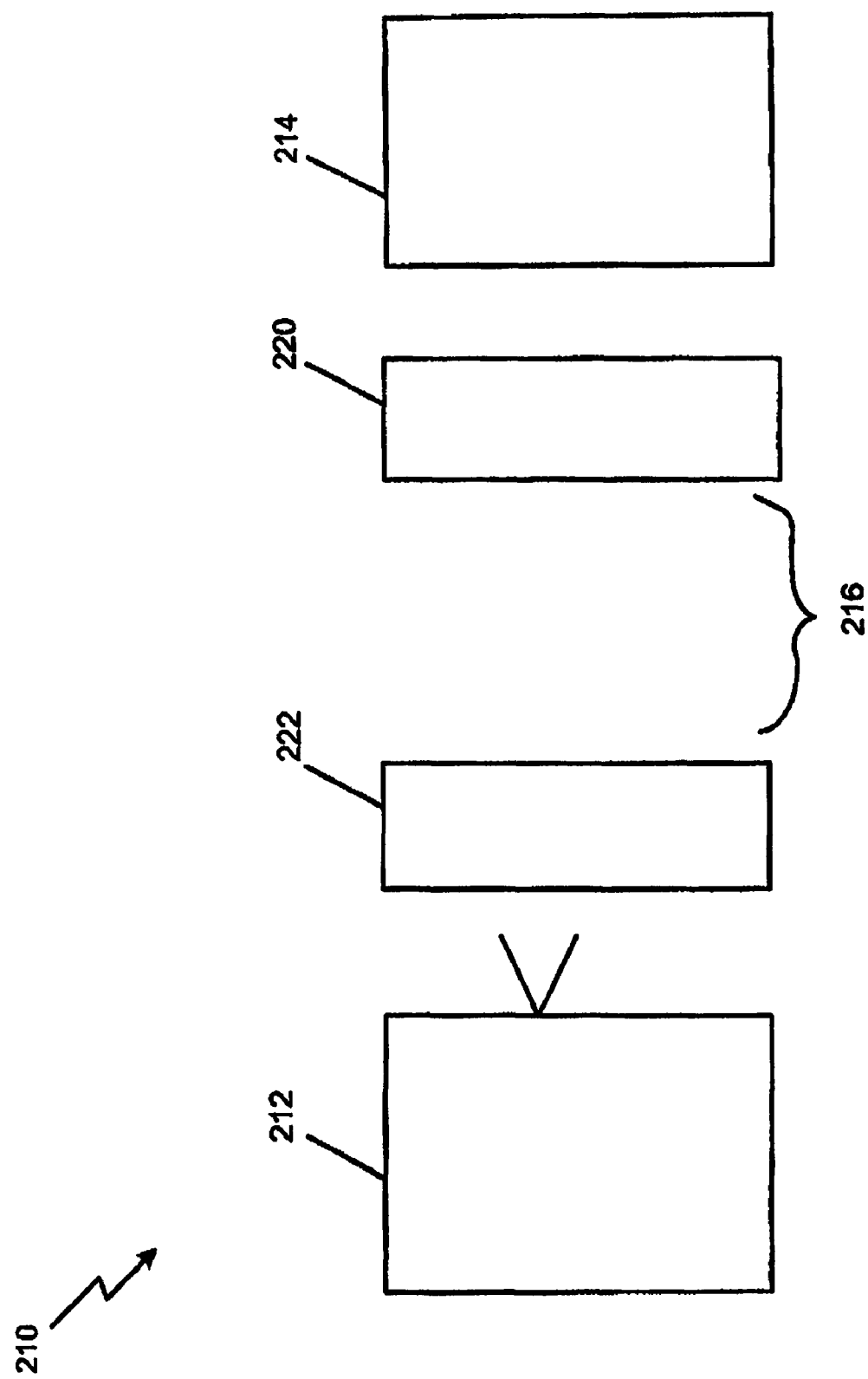
FIG. 3 is a schematic diagram of a substantially transparent object sensor within an automated assay processing system, in accordance with a third exemplary embodiment of the present invention.
Figure 4A:
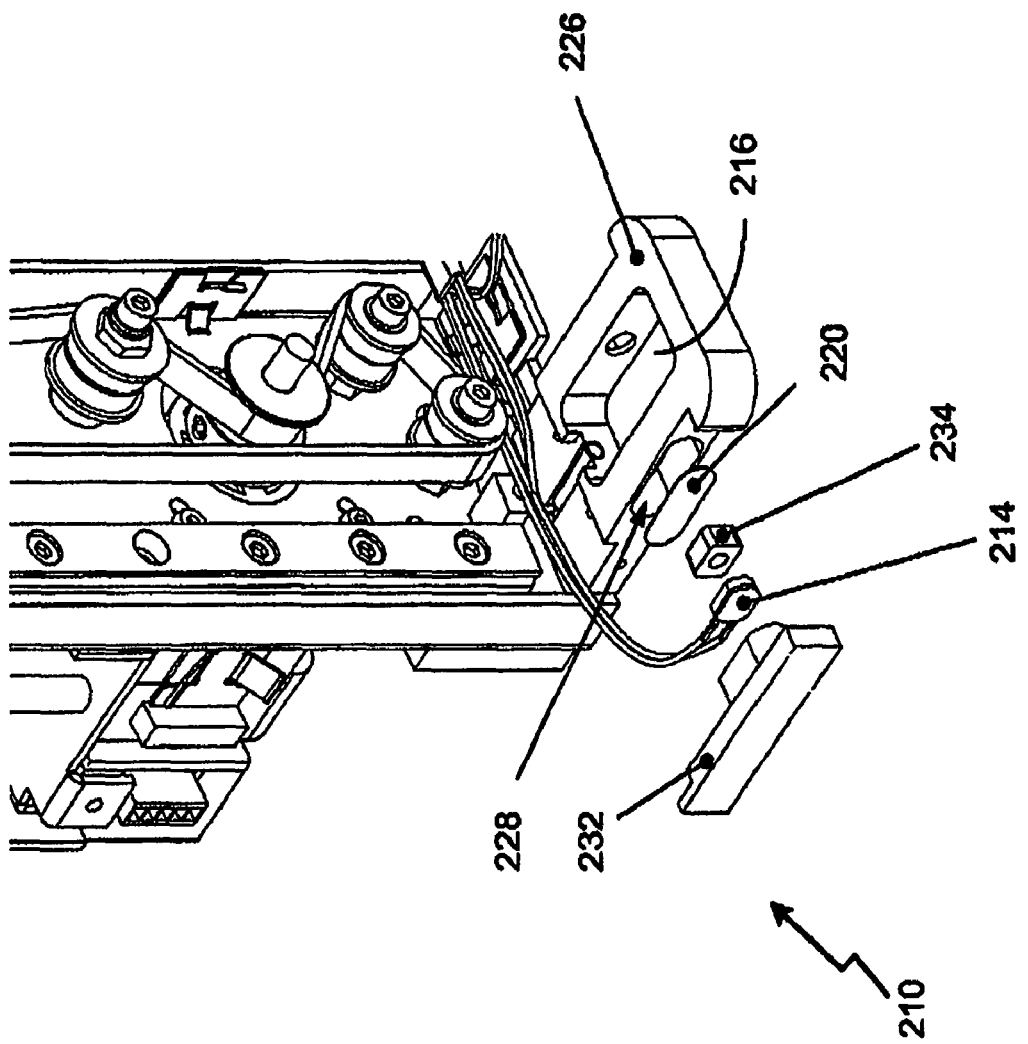
FIG. 4A is a first perspective view of the substantially transparent object sensor within an automated assay processing system of FIG. 3, in accordance with the third exemplary embodiment of the present invention.
Figure 4B:
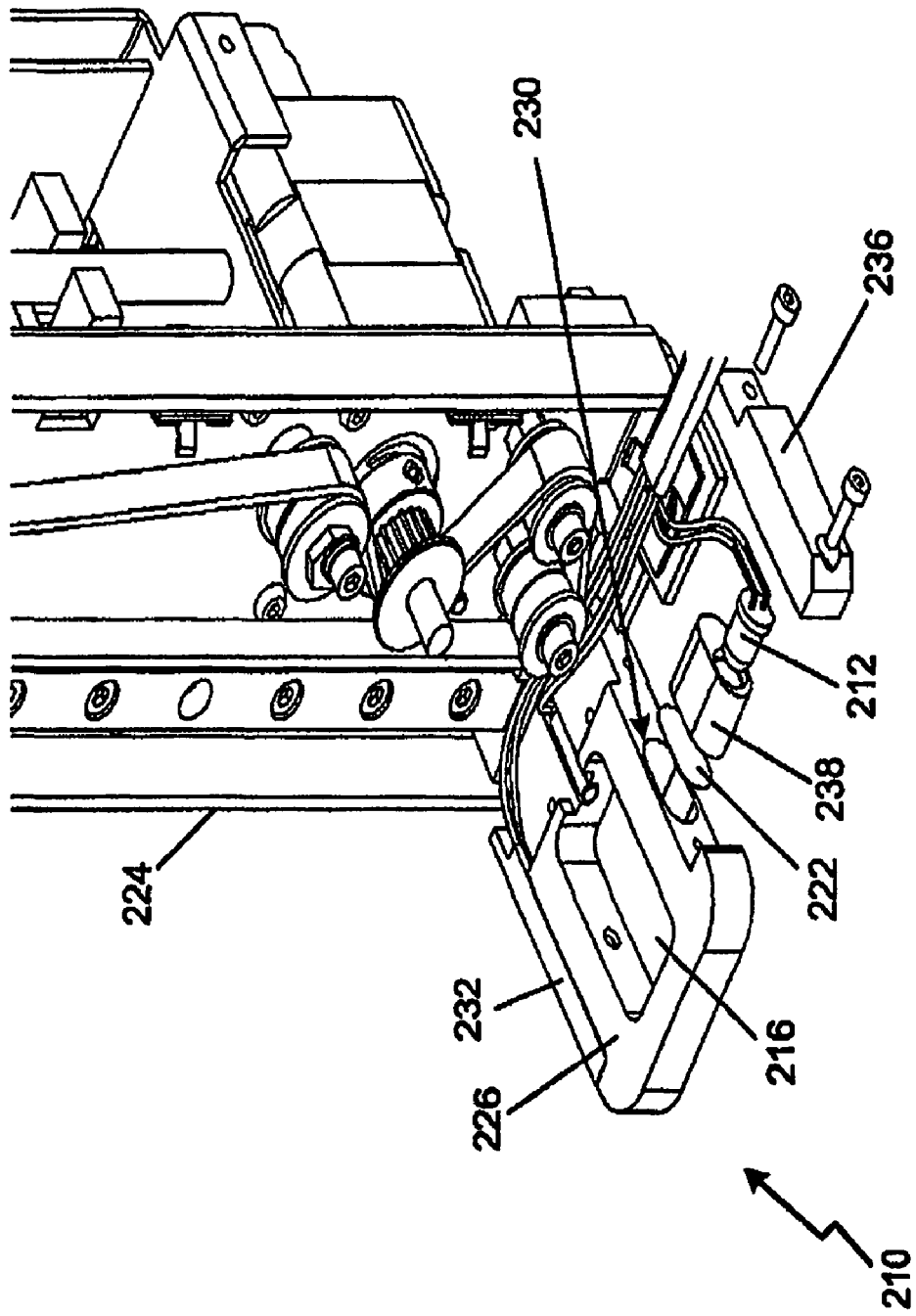
FIG. 4B is a second perspective view of the substantially transparent object sensor within an automated assay processing system of FIG. 3, in accordance with the third exemplary embodiment of the present invention.

FIG. 3 is a schematic diagram of a substantially transparent object sensor 210 within an automated assay processing system (not shown), in accordance with a third exemplary embodiment of the present invention. FIG. 4A is a first perspective view of the substantially transparent object sensor 210 located within an automated assay processing system 224 of FIG. 3, in accordance with the third exemplary embodiment of the present invention. FIG. 4B is a second perspective view of the substantially transparent object sensor 210 located within an automated assay processing system 224 of FIG. 3, in accordance with the third exemplary embodiment of the present invention. The substantially transparent object sensor 210 includes a radiation source 212 producing radiation at a predetermined bandwidth. A radiation receiver 214 is positioned to receive radiation from the radiation source 212. An opening 216 is formed between the radiation receiver 214 and the radiation source 212 sized to allow a substantially transparent object such as a sample or reagent tip to be slid between the radiation receiver 214 and the radiation source 212. A bandpass filter (not shown) is located between the radiation receiver 214 and the opening 216. The bandpass filter (not shown) is transmissive for radiation substantially within the predetermined bandwidth. Two polarizing filters 220, 222 are rotated relative to one another, and positioned between the radiation receiver 214 and the radiation source 212.

The radiation receiver 214 is mounted to the Z eject plate 226 by a diode retainer 232 and held in place by a diode retaining block 234. In the third exemplary embodiment, the bandpass filter is integral with the radiation receiver 214. More specifically, the radiation receiver 214 is a pass band filtered photodiode. Further, the radiation source 212 is a 660 nm LED and the radiation receiver 214 is a 660 nm pass band-filtered photodiode. The radiation source 212 is mounted to the Z eject plate 226 by an LED retainer 236 and held in place by an LED retaining block 238.

The substantially transparent object sensor 210 is mounted on a Z eject plate 226, which is a part of the automated assay processing system 224. As shown in FIGS. 4A and 4B, a first polarizing filter 220 and a second polarizing filter 222 are positioned between the radiation receiver 214 and the radiation source 212. Specifically, each polarizing filter 220, 222 is placed against each of the radiation receiver 214 and the radiation source 212. The first polarizing filter 220 is positioned at a first eject plate slot 228 proximate to the radiation receiver 214. The second polarizing filter 222 is positioned at a second eject plate slot 230 proximate to the radiation source 212. The polarizing filters 220, 222 are rotated relative to one other, preferably orthogonally (90°) to each other to substantially block the radiation from reaching the radiation receiver 214 in normal operation. The orthogonal positioning of the polarizing filters 220, 222 is respective of the filtering properties of the polarizing filters 220, 222 and not their physical shapes. However, when a substantially transparent object such as a sample or reagent tip is placed in the opening 216, formed within the Z eject plate 226, radiation from the radiation source 212 may be depolarized such that a material portion of the radiation is transmitted through the substantially transparent object and the first polarizing filter 220 to reach the radiation receiver 214.

Figure 5:
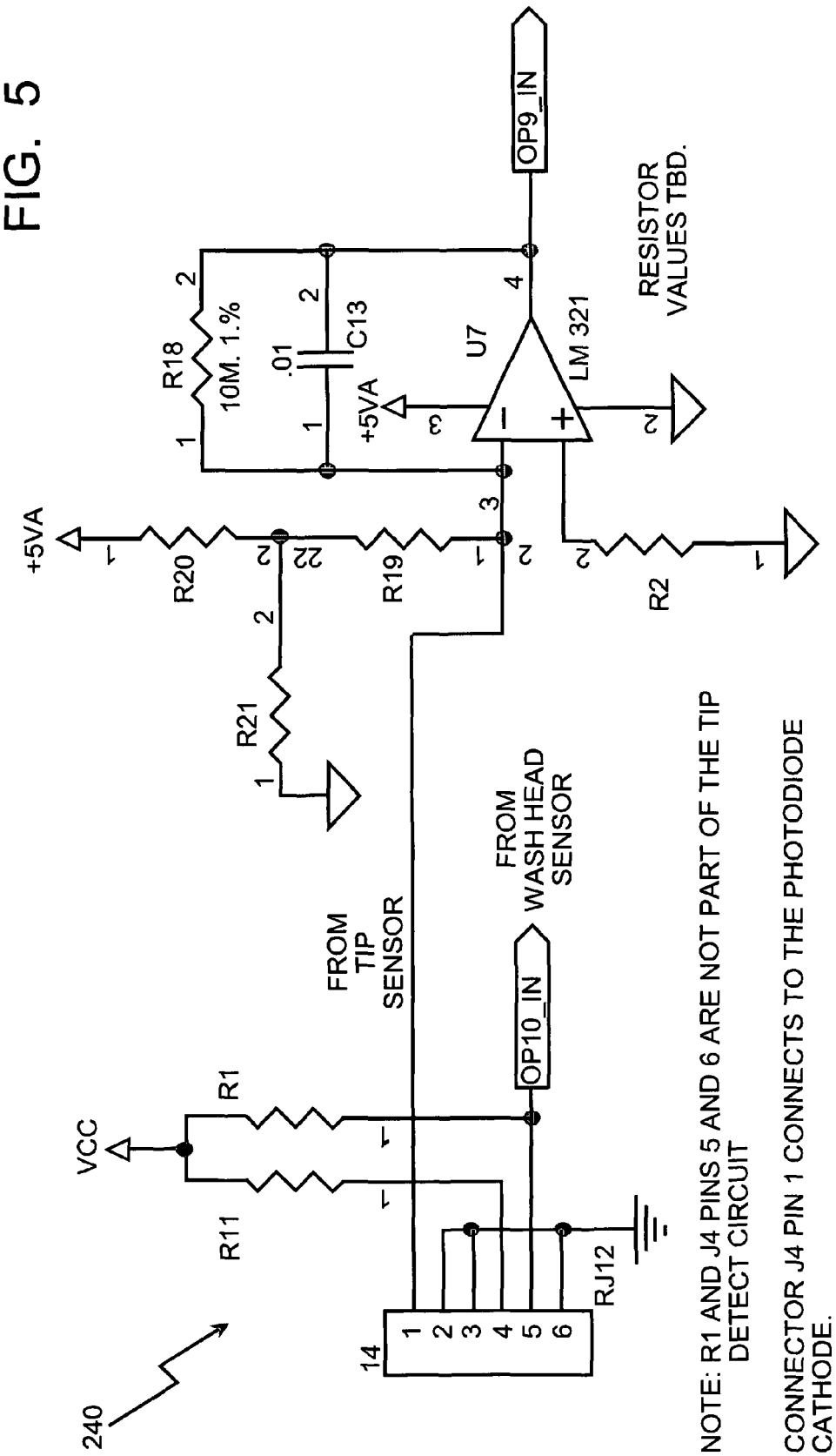
FIG. 5 is a circuit diagram for operation of the substantially transparent object sensor of FIG. 3, in accordance with the third exemplary embodiment of the present invention.

FIG. 5 is a circuit diagram 240 for operation of the substantially transparent object sensor 210 of FIG. 3, in accordance with the third exemplary embodiment of the present invention. The radiation source 212 (shown in FIG. 3) is driven by five volts DC at VCC through current limiting resistor R11. The negative current generated by the radiation receiver 214 (shown in FIG. 3) is applied to the summing junction of the operation amplifier OP1 formed by U7, R18, C13, and R2. Resistors R19, R20, and R21 generate a positive current applied to the summing junction to offset the radiation receiver 214 current generated by ambient light. Without a substantially transparent object positioned within the opening 216, an offset current is greater than the current generated by the radiation receiver 214, which causes the operational amplifier OP1 to be driven to ground. When a substantially transparent object such as a sample or reagent tip is positioned within the opening 216 (shown in FIG. 3), the current generated by the radiation receiver 214 is greater than an offset current and the difference is amplified by the operational amplifier OP1 to drive the output toward +5 VA. The two operational amplifier OP1 output states may be detected by digital logic as a logical 0 and 1, respectively.

Figure 6:
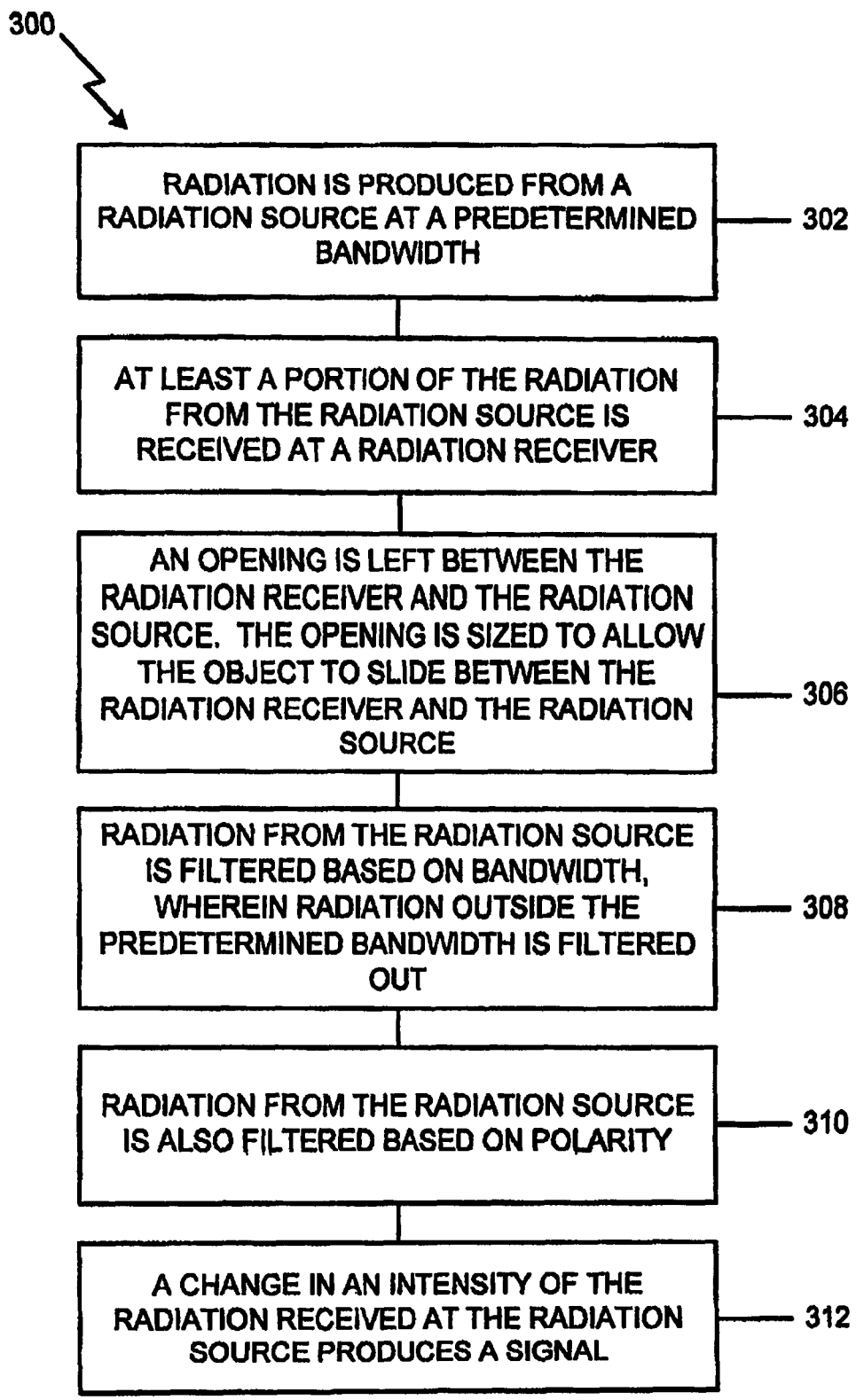
FIG. 6 is a flowchart illustrating a method of detecting a substantially transparent object in an automated assay processing system, in accordance with the first exemplary embodiment of the invention.

FIG. 6 is a flowchart 300 illustrating a method of detecting a substantially transparent object in an automated assay processing system, in accordance with the first exemplary embodiment of the invention.

As is shown by block 302, radiation is produced from a radiation source at a predetermined bandwidth. At least a portion of the radiation from the radiation source is received at a radiation receiver (block 304). An opening is left between the radiation receiver and the radiation source (block 306). The opening is sized to allow a sample or reagent tip to slide between the radiation receiver and the radiation source. Radiation from the radiation source is filtered based on bandwidth, wherein radiation outside the predetermined bandwidth is filtered out (block 308). Radiation from the radiation source is also filtered based on polarity (block 310). A change in an intensity of the radiation received at the radiation source produces a signal (block 312).

It should be emphasized that the above-described embodiments of the present invention, particularly, any "preferred" embodiments, are merely possible examples of implementations, merely set forth for a clear understanding of the principles of the invention. By way of example, process descriptions or blocks in flow charts should be understood as representing modules, segments, portions of code, or steps that include one or more instructions for implementing specific logical functions in the process, and alternate implementations are included within the scope of the present invention in which functions may be executed out of order from that shown or discussed, including substantially concurrently or in reverse order, depending on the functionality involved. Thus, variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. An automated assay processing system including a substantially transparent object sensor, comprising:
   a radiation source;
   a radiation receiver positioned to receive radiation from the radiation source;
   an opening formed between the radiation receiver and the radiation source sized to allow a substantially transparent object to slide between the radiation receiver and the radiation source;
   a first polarizing filter between the radiation receiver and the opening, a second polarizing filter, which is rotated relative to the first polarizing filter; and
   a detector coupled to the radiation receiver for detecting a change of intensity of radiation received at the radiation receiver when a substantially transparent object is interposed between the radiation receiver and the radiation source, and generates a signal which indicates either the presence or absence of a substantially transparent object when a change in intensity of radiation is detected, wherein the radiation source, the radiation receiver, the first polarizing filter, the second polarizing filter and the detector are all arranged in a linear path.

2. The system of claim 1, further comprising a Z-eject plate, wherein the radiation source and the radiation receiver are mounted within opposing sides of the Z eject plate.

3. The system of claim 1, further including a bandpass filter between the radiation receiver and the opening, wherein the bandpass filter is transmissive for radiation within a predetermined bandwidth.

4. The system of claim 3, wherein the radiation receiver is a pass band filtered photodiode.

5. The system of claim 1, wherein the radiation source is a 660 nm LED and the radiation receiver is a 660 nm pass band filtered photodiode.

6. The system of claim 1, wherein the first and second polarizing filters are orthogonally rotated relative to one another.

7. The system of claim 1, wherein the detector comprises a circuit in communication with the radiation receiver, wherein the circuit signals a change in an intensity of the radiation received by the radiation receiver.

8. The system of claim 7, wherein the circuit signals the presence of a substantially transparent object with an output state that can be detected by digital logic as one of either logical "0" or logical "1", and the absence of a substantially transparent object is signaled by an output state that can be detected by digital logic as the opposite state from the output state that signals the presence of a substantially transparent object.

9. The system of claim 1, wherein the automated assay processing system is an Enzyme-Linked ImmunoSorbent Assay processing apparatus, and the substantially transparent object is a sample or reagent tip.

10. The system of claim 1, wherein the second polarizing filter is rotated at a fixed 90 degree orientation relative to the first polarizing filter.

11. A method of detecting a substantially transparent object in an automated assay processing system, the method comprising the steps of:
    directing radiation from a radiation source through a first radiation polarizer;
    directing the polarized radiation through a second polarizer which is rotated relative to the first polarizer, to a radiation receiver;
    interposing a substantially transparent object between the radiation receiver and the radiation source;
    detecting a change in an intensity of the radiation received at the radiation receiver;
    associating the change in intensity of the radiation received at the radiation receiver with the presence of a substantially transparent object between the radiation receiver and the radiation source, wherein the radiation source, the radiation receiver, the first radiation polarizer, and the second radiation polarizer are all arranged in a linear path; and
    generating a signal which indicates either the presenceor abscence of a substantially transparent object.

12. The method of claim 11, wherein the automated assay processing system comprises an Enzyme-Linked ImmunoSorbent Assay processing apparatus, and the substantially transparent object comprises a sample or reagent tip.

13. The method of claim 11, wherein the second polarizer is rotated at a fixed 90 degree orientation relative to the first polarizer.

* * * * *

UNITED STATES PATENT AND TRADEMARK OFFICE
CERTIFICATE OF CORRECTION

PATENT NO. : 7,777,211 B2  
APPLICATION NO. : 11/832578  
DATED : August 17, 2010  
INVENTOR(S) : Taylor It is certified that error appears in the above-identified patent and that said Letters Patent is hereby corrected as shown below:

In the Claims:

Claim 11, Col. 6, line 38 "the presenceor abscence" should be --the presence or absence--.

Signed and Sealed this  
Ninth Day of July, 2013

Teresa Stanek Rea  
*Acting Director of the United States Patent and Trademark Office*